United States Patent [19]

Jessel, Jr. et al.

[11] Plant 4,473

[45] Oct. 30, 1979

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 952,242

[22] Filed: Oct. 17, 1978

[51] Int. Cl.[2] ..... A01H 5/00

[52] U.S. Cl. ..... Plt./77

[58] Field of Search ..... Plt./77–78

*Primary Examiner*—Robert E. Bagwill

*Attorney, Agent, or Firm*—Donald D. Jeffery

[57] ABSTRACT

A chrysanthemum plant known by the cultivar name Cambria and particularly characterized as to uniqueness by the combined characteristics of flat capitulum form; spider capitulum type; ivory white ray floret color, devoid of pink discoloration; diameter across face of capitulum ranging from 175 to 225 mm. at maturity; uniform eight weak photoperiodic flowering response to short days; and tall plant height.

1 Drawing Figure

The present invention comprises a new and distinct cultivar of *Chrysanthemum morifolium,* Ramat., hereinafter referred to by the cultivar name Cambria.

Cambria is a product of a planned breeding program which had the objective of creating new chrysanthemum cultivars with large sized spider capitulum type, tall height, and eight or nine week flowering response. Such traits in combination were not present in previously available commercial cultivars.

Cambria was originated from a cross made in a controlled breeding program in Barberton, Ohio in 1972. The female parent was White Spider 2275 (unpatented; commercially available), a white spider. The male parent was Yellow Daisy Pot 332 (unpatented; commercially available), a yellow spooned daisy. The parentage of White Spider 2275 and Yellow Daisy Pot 332 is unknown to the present inventors.

Cambria was discovered and selected as one flowering plant within the progeny of the stated cross by Walter H. Jessel, Jr. and William E. Duffett on Mar. 26, 1973 in a controlled environment in Barberton, Ohio.

The first act of asexual reproduction of Cambria was accomplished when vegetative cuttings were taken from the initial selection in June, 1973 in a controlled environment in Barberton, Ohio by a technician working under formulations established and supervised by Walter H. Jessel, Jr. and William E. Duffett. Continued asexual reproduction by vegetative cuttings for evaluative tests in flowering and stock programs in conjunction with horticultural examination of selected units initiated Nov. 13, 1973 has demonstrated that the combination of characteristics as herein disclosed for Cambria are firmly fixed and are retained through successive generations of asexual reproduction.

Cambria has not been observed under all possible environmental conditions. The phenotype may vary significantly with variations in environment such as temperature, light intensity, and daylength. The following observations, measurements, and comparisons describe plants grown in Barberton, Ohio and in Salinas, Calif. under greenhouse conditions which approximate those generally used in commercial practice.

The following traits have been repeatedly observed and are determined to be basic characteristics of Cambria which in combination distinguish this chrysanthemum as a new and distinct cultivar:

(1) Flat capitulum form.

(2) Spider capitulum type.

(3) Ivory white ray floret color, devoid of pink discoloration.

(4) Diameter across face of capitulum ranging from 175 to 225 mm. at maturity.

(5) Uniform eight week photoperiodic flowering response to short days.

(6) Tall plant height (attains flowered plant height of 90 to 95 cm. with no long days for May through October flowerings).

The accompanying photographic drawing shows typical inflorescense and foliage characteristics of Cambria, with the colors being as nearly true as possible with illustrations of this type.

Of the many commercial cultivars known to the present inventors, the most similar existing cultivar in comparison to Cambria is Super White (unpatented), a sport of the parental cultivar, White Spider 2275. Reference is made to attached Chart A which compares certain characteristics of Cambria to those same characteristics of Super White. General comparisons are as follows:

In comparison to Super White, Cambria has less pinking coloration of ray florets with a cool finish (below 60° night temperatures), greater diameter across face of capitulum, and taller plant height. The ray floret color (at 60° night temperature and above), the capitulum type, capitulum form, and the flowering response period of Cambria is similar to those same characteristics of Super White.

In the following description, color references are made to A Limit Color Cascade, by the Munsell Company, 1972 edition. The color values were determined between 9:30 and 10:00 A.M. on May 17, 1978 under 90 foot-candle light intensity at Salinas, Calif.

Botanical classification: *Chrysanthemum morifolium,* Ramat., cv. Cambria.

I. INFLORESCENCE

A. Capitulum:

*Form.*—Flat.

*Type.*—Spider.

*Diameter across face.*—175 to 225 mm.

B. Corolla of ray florets:

*Persistence.*—Resists shatter.

*Color (abaxial).*—Immature 21-2 to 25-2 to mature 25-1 to 25-3.

*Color (adaxial).*—Approximately 25-1.

C. Reproductive organs:

*Androecium.*—Present disc florets only; scant to few; scant pollen.

*Gynoecium.*—Present both ray and disc florets.

II. PLANT

A. General appearance: semi-upright branching pattern; tall plant height, attaining height of 92 cm. in June flowerings with no long days.

B. Foliage:

*Color (abaxial).*—Approximately 20-15.

*Color (adaxial).*—Approximately 20-13 to 20-14.

COMPARISON OF CAMBRIA AND SUPER WHITE

| Cultivar | Ray Floret Color | Capitulum Form And Type |
|---|---|---|
| Cambria | Ivory white | Flat spider |
| Super White | Ivory white tinging pink | Flat spider |

-continued

COMPARISON OF CAMBRIA AND SUPER WHITE at cooler temperatures.

| Cultivar | Diameter Across Face of Capitulum | Plant Height | Flowering Response Period |
|---|---|---|---|
| Cambria | 175 to 225 mm. | Tail, from 90 to 95 cm. | 8 week |
| Super White | 150 to 175 mm. | Short, from 70 to 80 cm. | 8 week |

Comparisons Made Of Disbudded Single Stem Plants Grown In Barberton, Ohio And Salinas, California.

We claim:

1. A new and distinct cultivar of *Chrysanthemum morifolium,* Ramat., plant known by the cultivar name Cambria and particularly characterized as to uniqueness by the combined characteristics of flat capitulum form; spider capitulum type; ivory-white ray floret color, devoid of pink discoloration; diameter across face of capitulum ranging from 175 to 225 mm. at maturity; uniform eight week flowering response to short days; and tall plant height.

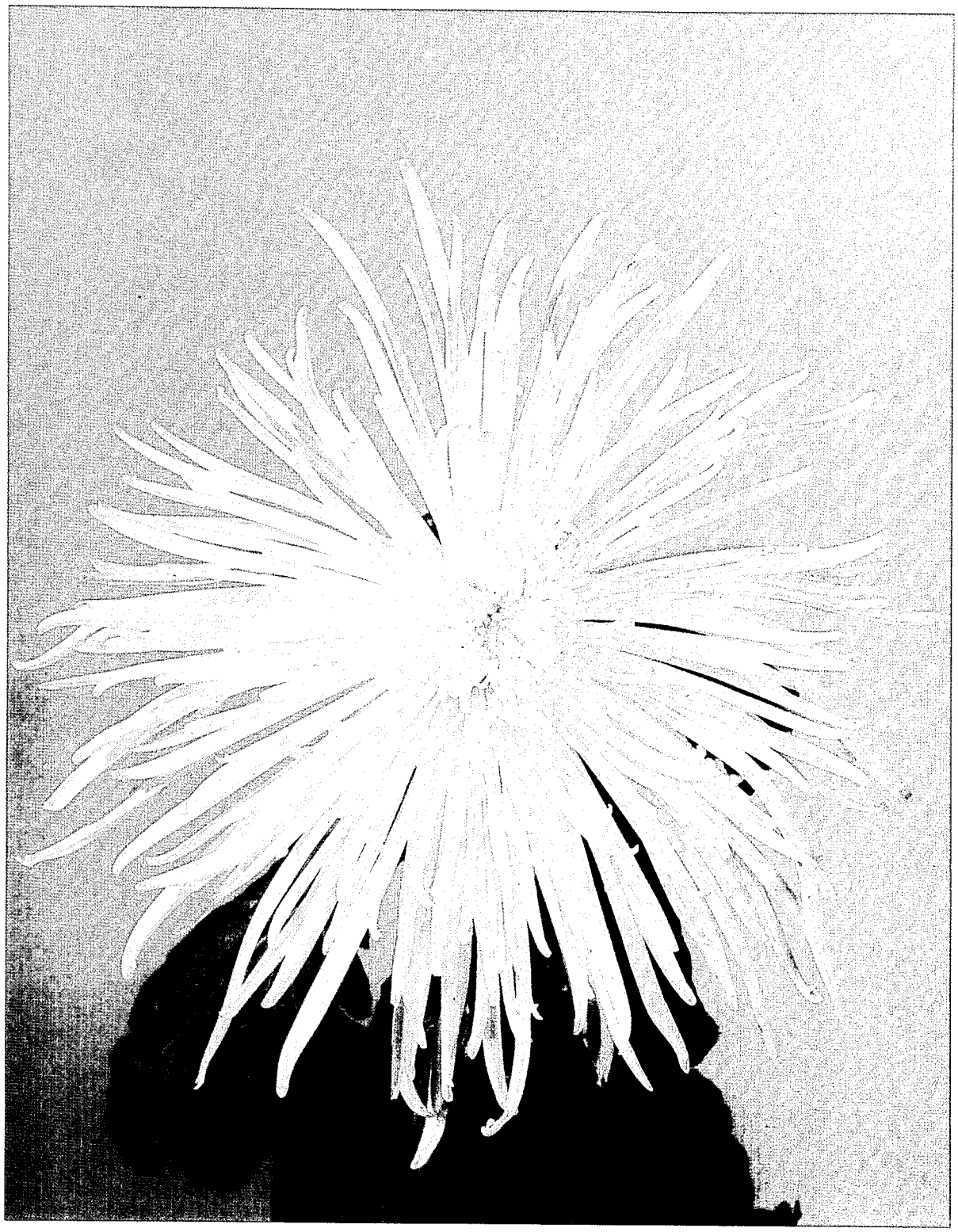

* * * * *